(12) United States Patent
Chen et al.

(10) Patent No.: US 10,639,336 B1
(45) Date of Patent: May 5, 2020

(54) USE OF A PROBIOTIC COMPOSITION FOR PREVENTING STROKE AND AMELIORATING THE SEVERITY OF STROKE

(71) Applicant: GenMont Biotech Incorporation, Tainan (TW)

(72) Inventors: Yi-Hsing Chen, Tainan (TW); Wan-Hua Tsai, Kaohsiung (TW); Shiang-Suo Huang, Taipei (TW); Yi-Hsin Wang, Tainan (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 0 days.

(21) Appl. No.: 16/435,944

(22) Filed: Jun. 10, 2019

(51) Int. Cl.
*A61P 1/14* (2006.01)
*A61K 35/747* (2015.01)
*A61K 35/00* (2006.01)

(52) U.S. Cl.
CPC .............. *A61K 35/747* (2013.01); *A61P 1/14* (2018.01); *A61K 2035/115* (2013.01)

(58) Field of Classification Search
None
See application file for complete search history.

(56) References Cited

U.S. PATENT DOCUMENTS

| 8,298,526 | B2 * | 10/2012 | Leu | C12R 1/225 |
| | | | | 424/93.1 |
| 9,301,983 | B2 * | 4/2016 | Huang | A61K 35/747 |
| 2009/0274672 | A1 * | 11/2009 | Yu | A61K 35/747 |
| | | | | 424/93.45 |

* cited by examiner

*Primary Examiner* — Padmavathi Baskar
(74) *Attorney, Agent, or Firm* — WPAT, PC

(57) ABSTRACT

The present invention provides a composition for preventing stroke and ameliorating the severity of stroke and comprises an effective dose of *Lactobacillus reuteri* GMNL-89 and *Lactobacillus paracasei* GMNL-133; the accession number of *Lactobacillus reuteri* GMNL-89 is CCTCC M207154 and the accession number of *Lactobacillus paracasei* GMNL-133 is CCTCC M2011331. The composition can be taken as a dietary supplement and be given continuously after a stroke, and said composition has the effects of ameliorating cerebral infarction, motor function, and intestinal microbiota after a stroke.

6 Claims, 5 Drawing Sheets

USE OF A PROBIOTIC COMPOSITION FOR PREVENTING STROKE AND AMELIORATING THE SEVERITY OF STROKE

BACKGROUND OF THE INVENTION

Field of the Invention

The present disclosure describes a use of *Lactobacillus* isolated strains for preventing stroke and ameliorating the severity of stroke.

Description of the Prior Art

Cerebrovascular disease consistently ranks among the top ten leading causes of death in the world. The damage caused by cerebral infarction can affect the whole body, causing disability and death, and thus the disease is a huge burden for social medical resources and families. The incidence of ischemia stroke is the highest in cerebrovascular diseases, accounting for 80% of the total stroke patients. The most important strategy for treating ischemic stroke is the thrombolytic therapy which reopens the infarct zone, restores blood flow, and reduces the size of the infarct zone in patient with ischemic stroke. However, in recent years, studies have shown that significant amount of free radicals or reactive oxygen species are produced in the ischemic region after blood flow is restored and the region is reperfused, which causes more serious damage to the ischemic cells and results in ischemia-reperfusion injury. Meanwhile, blood reperfusion injury will induce oxidative stress, which then causes DNA damage and lipid peroxidation and will subsequently increase the secretion of cytokines and chemokines and lead to infiltration of a large number of white blood cells in the infarct zone, which will trigger inflammatory responses and induce apoptosis of neurons and impair nerve function.

The microbial flora in the intestine interacts with the central nervous system, the autonomic nervous system, and the immune system, and can form a microbiome-gut-brain axis through three pathways (immunity, neuroendocrine, and vagus nerve) of the gut-brain axis, which has a major impact on the central nervous system, that is, maintaining the normal intestinal microflora can help retain the intestinal barrier function, enhance intestinal immunity and reduce excessive inflammatory responses.

The intestinal microbiota is highly correlated with stroke and cerebral damage. Studies have indicated that the balance of intestinal flora was destroyed in the middle cerebral artery occlusion (MCAO) mouse mode, accompanied by reduced intestinal barrier function and increased intestinal permeability, which eventually worsened stroke outcome. In addition, in the MCAO mouse model, some bacteria that cause intestinal inflammation are increased, for example, *Bacteroides, Escherichia Shigella, Haemophilus, Eubacterium nodatum* group, *Collinsella, Enterococcus, Proteus, Alistipes, Klebsiella, Shuttleworthia*, and *Faecalibacterium* . . . etc.; furthermore, some of the good bacteria that regulate the immune response and enhance the barrier function of the intestinal epithelial cells are reduced, such as *Alloprevotella, Ruminococcaceae, Oscillospira, Lachnospiraceae* NK4B4 group, *Akkermansia*, and *Megasphaera*.

Pretreatment of mice with broad-spectrum antibiotics reduces the size of the infarct zone in the mice with ischemic stroke after a surgery. The mice treated with antibiotics activate regulatory T cells (Tregs) and decrease IL-17+γδ T cells, thereby reducing accumulation of the downstream related chemokines in the brain and ameliorating the severity of stroke. However, antibiotics cannot be used as a maintenance or for prevention of diseases, and excessive use of antibiotics can lead to many side effects. Therefore, the better strategy is to prevent ischemic stroke in the future by using probiotics that are safe and have no side effects to regulate intestinal flora, maintain intestinal barriers, and reduce excessive inflammatory responses.

In addition, studies have found that, in the animal model of bilateral common carotid artery ligation followed by reperfusion, administration of *Clostridium butyricum* ($1\times10^9$ CFU/kg) reduces oxidative stress and apoptosis caused by cerebral ischemia-reperfusion injury and achieves the effect of neuroprotection. Yet, bilateral common carotid artery ligation is not the main cause of clinical ischemic stroke. Most of the clinical ischemic stroke is caused by ischemia in the middle cerebral artery or its branches, but no study has been performed to evaluate the protective effect of probiotics in the occurrence of ischemic stroke and its correlation with intestinal microbiota.

This invention utilizes a middle cerebral artery ligation (MCAO) mouse model to simulate the occurrence of ischemic stroke and evaluate whether functional probiotics have preventive and protective effects and their correlation with intestinal microbiota. Because the research on probiotics in preventing stroke and ameliorating the symptoms after a stroke is not common, it is urgent to find effective probiotics.

SUMMARY OF THE INVENTION

In one aspect, the present invention provides a composition for preventing stroke and ameliorating the severity of stroke, which comprises an effective dose of *Lactobacillus reuteri* GMNL-89 and *Lactobacillus paracasei* GMNL-133, wherein the accession number of *Lactobacillus reuteri* GMNL-89 is CCTCC M207154 and the accession number of *Lactobacillus paracasei* GMNL-133 is CCTCC M2011331.

According to the purpose of the aforementioned invention, the composition is taken as a dietary supplement for a normal person or after a stroke.

In another aspect, the present invention provides a use of a probiotic composition for preventing stroke and ameliorating the severity of stroke, wherein the probiotic composition is selected from the groups consisting of *Lactobacillus reuteri* GMNL-89, and *Lactobacillus paracasei* GMNL-133; wherein the accession number of *Lactobacillus reuteri* GMNL-89 is CCTCC M207154 and the accession number of *Lactobacillus paracasei* GMNL-133 is CCTCC M2011331.

According to the purpose of the aforementioned invention, wherein ameliorating stroke is ameliorating ischemic stroke.

According to the purpose of the aforementioned invention, wherein ameliorating the severity of stroke is reduce the size of the infarct zone caused by stroke in the brain.

According to the purpose of the aforementioned invention, wherein ameliorating the severity of stroke is ameliorating the recovery state of the patient after a stroke.

According to the purpose of the aforementioned invention, wherein the recovery states of the patient is motor function.

According to the purpose of the aforementioned invention, wherein the dose of the probiotics is $1\times10^7 \sim 1\times10^{10}$ live bacteria per day.

In still another aspect, the present invention provides a use of a probiotic composition for ameliorating the intestinal microbiota after a stroke, wherein the probiotic composition is selected from the groups consisting of *Lactobacillus reuteri* GMNL-89 and *Lactobacillus paracasei* GMNL-133; wherein the accession number of *Lactobacillus reuteri* GMNL-89 is CCTCC M207154 and the accession number of *Lactobacillus paracasei* GMNL-133 is CCTCC M2011331.

According to the purpose of the aforementioned invention, wherein ameliorating the intestinal microbiota after a stroke is increasing the richness of the good bacteria.

According to the purpose of the aforementioned invention, wherein the good bacteria is *Ruminococcaceae* or *Oscillospira*.

According to the purpose of the aforementioned invention, the dose of the probiotics is $1 \times 10^7 \sim 1 \times 10^{10}$ live bacteria per day.

In summary, the probiotic composition of the present invention can reduce the size of the infarct zone, restore motor function, and ameliorate the intestinal microbiota by increasing the good bacteria of an individual after stroke, thereby achieving the effect of preventing stroke and ameliorating the severity of stroke.

DETAILED DESCRIPTION OF THE PREFERRED EMBODIMENT

All technical and scientific terms used in the invention, unless otherwise defined, are the common general knowledge to a person having ordinary skill in the art. The composition described in the disclosure is comprising of, but not limited to, food, drinks, functional food, additives of animal drinking water, additives of animal feed, medical composition for animal and human, food additives, and drink additives that are applicable to the use of the present invention. To fully understand the purpose, features and functions of present invention, following examples are provided with embodiments to explain the details of present invention. However, it should be noted that the invention is not limited to the preferred embodiments shown.

*Lactobacillus reuteri* GMNL-89 (hereinafter referred to as GMNL-89) is deposited in Taiwan Food Industry Research and Development Institute, the date of deposition is Nov. 14, 2006, and the accession number is BCRC910340 and is also deposited in China Center for Type Culture Collection (CCTCC), the date of deposition is Nov. 19, 2007, and the accession number is CCTCC M207154.

*Lactobacillus paracasei* GMNL-133 (hereinafter referred to as GMNL-133) is deposited in Taiwan Food Industry Research and Development Institute, the date of deposition is Jul. 5, 2010, and the accession number is BCRC910520 and is also deposited in China Center for Type Culture Collection (CCTCC), the date of deposition is Sep. 26, 2011, and the accession number is CCTCC M2011331.

Method

Figure 1A:
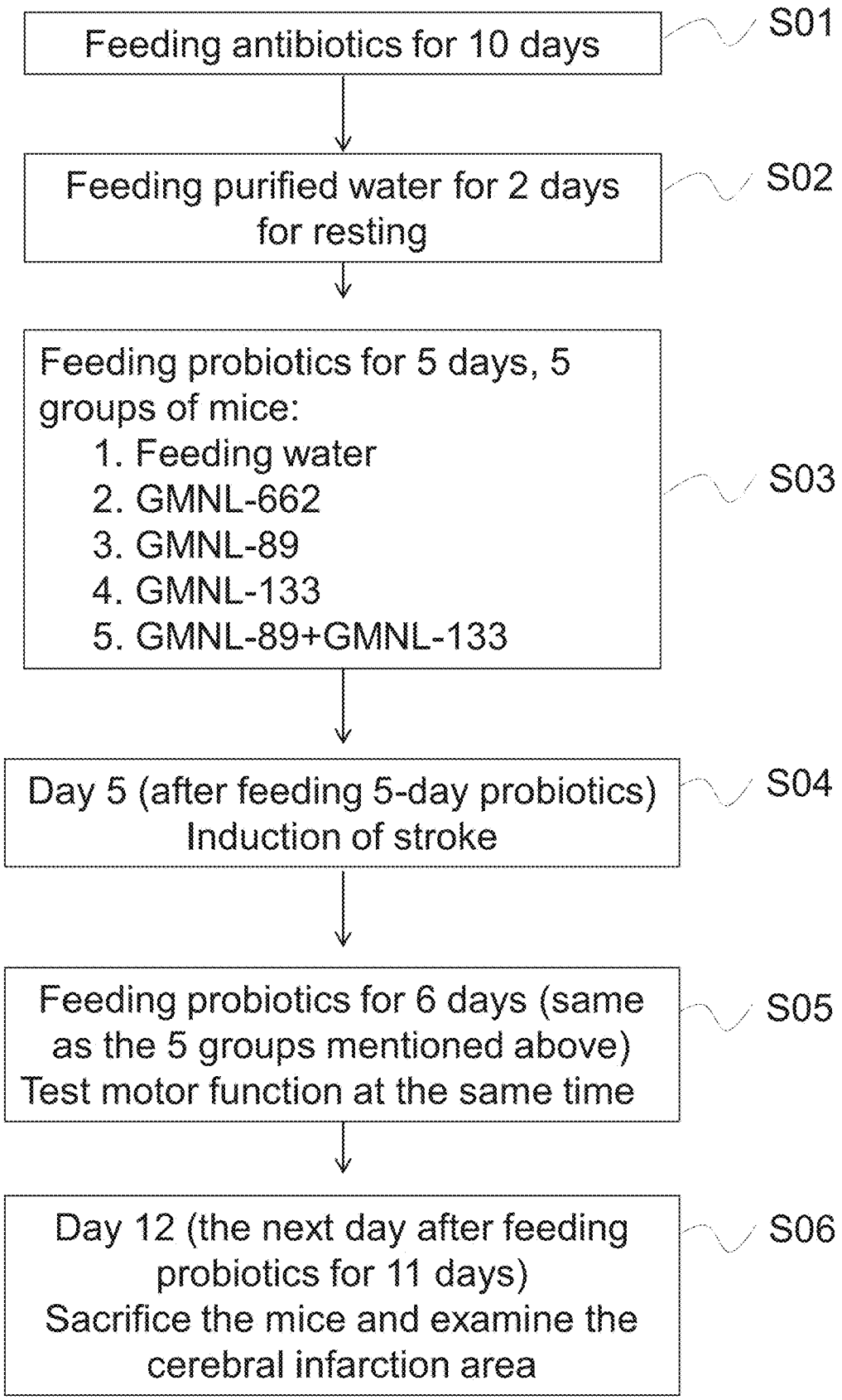
FIG. 1A shows the experimental process.
Figure 1B:
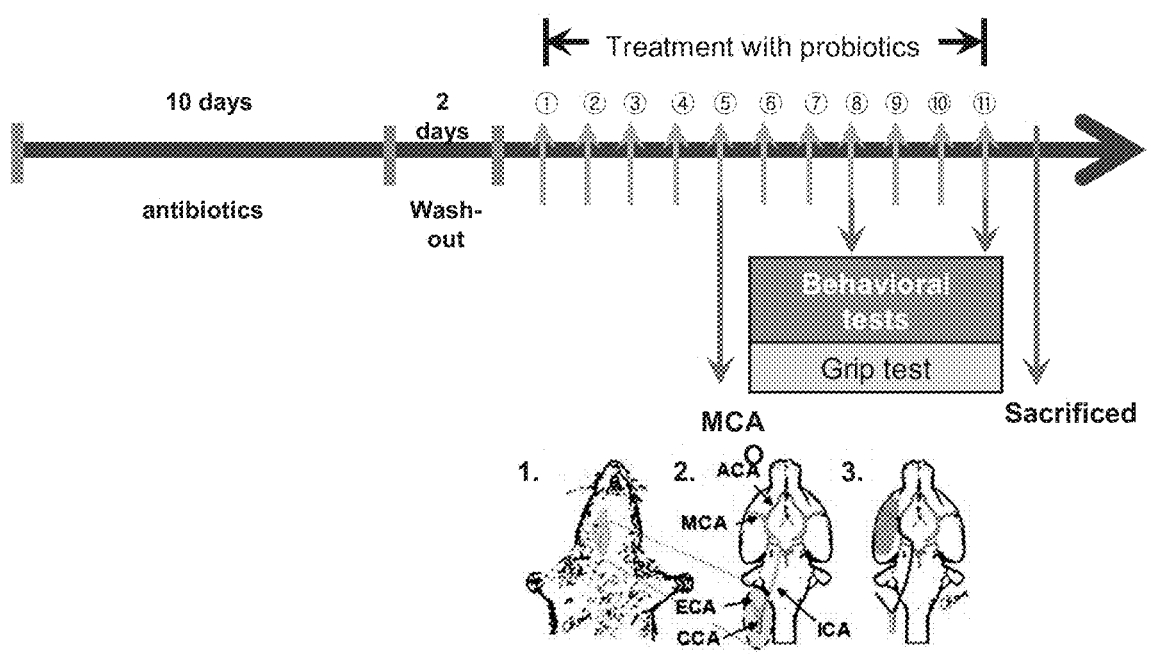
FIG. 1B shows the experimental process and surgery model.

Experimental stroke animal model: The experimental procedure is shown in FIG. 1A and FIG. 1B (above). Male C57BL/6 mice (8-12 weeks; 22-28 g) were used in the study. The animals were purchased from BioLASCO Taiwan Co., Ltd. and housed in a climate-controlled environment, 25±4° C. 55±5% humidity with a 12 h light/dark cycle and with free access to food and water.

The mice were given antibiotic sulfamethoxazole (0.8 mg/ml) and trimethoprim (0.16 mg/ml) for 10 days followed by purified water for 2 days before receiving the surgery of middle cerebral artery ligation. The mice were then divided into different groups:

Vehicle group: water only;

GMNL-662: $8.2 \times 10^7$ CFU (low dose) or $8.2 \times 10^8$ CFU (high dose) per kg per mouse via gavage;

GMNL-89: $8.2 \times 10^7$ CFU (low dose) or $8.2 \times 10^8$ CFU (high dose) per kg per mouse via gavage;

GMNL-133: $8.2 \times 10^7$ CFU (low dose) or $8.2 \times 10^8$ CFU (high dose) kg/mouse via gavage;

GMNL-89+GMNL-133 (1:1): $8.2 \times 10^7$ CFU (GMNL-89+GMNL-133 (1:1, low dose) or $8.2 \times 10^8$ CFU (GMNL-89+GMNL-133, 1:1, high dose).

The lactic acid bacteria are prepared by dissolving the lyophilized powder of the strain in sterile water, mixing it thoroughly, the mice were fed once a day by gavage for 4 consecutive days, the surgery of middle cerebral artery ligation was performed on Day 5 after feeding, followed by probiotics feeding for 6 days. The mice were evaluated for 7 days after receiving the middle cerebral artery ligation surgery. The animals were continuously fed with water or the solution of lactic acid bacteria for 11 days.

Ligation of the right middle cerebral artery (MCA) causes ischemia in the right cerebral cortex and the procedure is shown in FIG. 1B (below). The mice were anesthetized with 2% isoflurane and then the hair of the neck and head was shaved. An incision was made in the midline of the neck to locate the common carotid artery (CCA) on both sides of the trachea. After separating the CCA, the C57BL/6 mice were placed in lateral position. Next, an incision was made from left canthux to pinna to separate the muscles, a hole was drilled in the joint of the zygoma bone and the squamosal bone with a bone drill to form a bone window with a diameter of about 3 mm. A fine tweezer was used to open the dura under the operating microscope to expose the right middle cerebral artery. The bipolar electrocautery was used to block the blood flow of MCA and then the vessel was clamped to stop blood flow for 20 minutes to induce local ischemic injury in the central nervous system of the mice. The clamp was then released and the blood vessel was reperfused before closing the wound with 4/0 suture. The mice were placed on an electric blanket during the operation and after surgery to maintain constant body temperature. Evaluation of cerebral infarction injury: On Day 7 after surgery, the animals were sacrificed after anesthesia, and the brains were removed, washed with PBS, and checked for bleeding or infection. The animals were excluded if the mice developed abnormalities in the cerebral vascular sites or the anatomical location in middle cerebral artery was abnormal. The brain tissue of the mouse was placed in a cold physiological solution for 10 minutes and then be sectioned into slices of a thickness of 1 mm in the mold for sectioning before being soaked in 2% 2,3,5 Triphenyltetrazolium chloride (TTC) at 37° C. in the dark for 30 minutes. The tissue sample was then fixed with 10% Formaldehyde for 24 hours and then scanned. The image processing system (Image J software, National Institutes of Health (NIH), USA) was used to calculate the area of cerebral infarction injury. The milky white area or the necrotic and liquefied area (defective area) all belong to the area of cerebral infarction injury.

Animal Behavior Assessment: The time points for the behavioral assessment are scheduled for the day before stroke induction as well as on Day 3 and Day 6 after stroke induction. The Grip Test was used to test the fore limb and hind limb grip strength and balance of the mice. The test is performed by picking up the tail of the mouse and only allow its forepaws to attach to the 50 cm-long metal grid which is placed 20 cm above the table. The time of the test is 30 seconds. Table 1 is the scoring standard for the Grip Test.

TABLE 1

Grip Test Scoring Standard

| Score | Scoring standard |
|---|---|
| 0 | Falls off within 30 seconds |
| 1 | Holding onto the metal grid in any possible way for 30 seconds |
| 2 | All four limbs are holding onto the metal grid and for at least 5 seconds |
| 3 | All four limbs and the tail are holding onto the metal grid and for at least 5 seconds |
| 4 | All four limbs and the tail are holding onto the metal grid and climbing on the grid for at least 5 seconds |
| 5 | Climbing on the metal grid within 30 seconds and escape successfully |

Microbiota analysis: The fresh feces of the mice were collected at the end of the study. After the fecal DNA was extracted, the V3-V4 region of 16S rRNA was sequenced using Illumina MiSeq System Sequencing (2×301 bp paired-end), and changes in fecal microbiota of different groups (including all levels from phylum to species) were then analyzed by comparison. The four groups subjected to microbiota analysis were: the vehicle group and the three high-dose groups including GMNL-89 ($8.2 \times 10^8$ CFU/kg), GMNL-133 ($8.2 \times 10^8$ CFU/kg), and GMNL-89+GMNL-133 ($8.2 \times 10^8$ CFU/kg).

Statistics: Data were expressed as mean±SEM. Improvements in the infarct zone and improvement in behavioral dysfunction were analyzed by one-way analysis of variance (ANOVA) followed by Student's t-test to determine whether the differences between the vehicle group and groups received different concentrations of probiotics are significant. The results with a p<0.05 are considered to have a significant difference (*).

Figure 2:
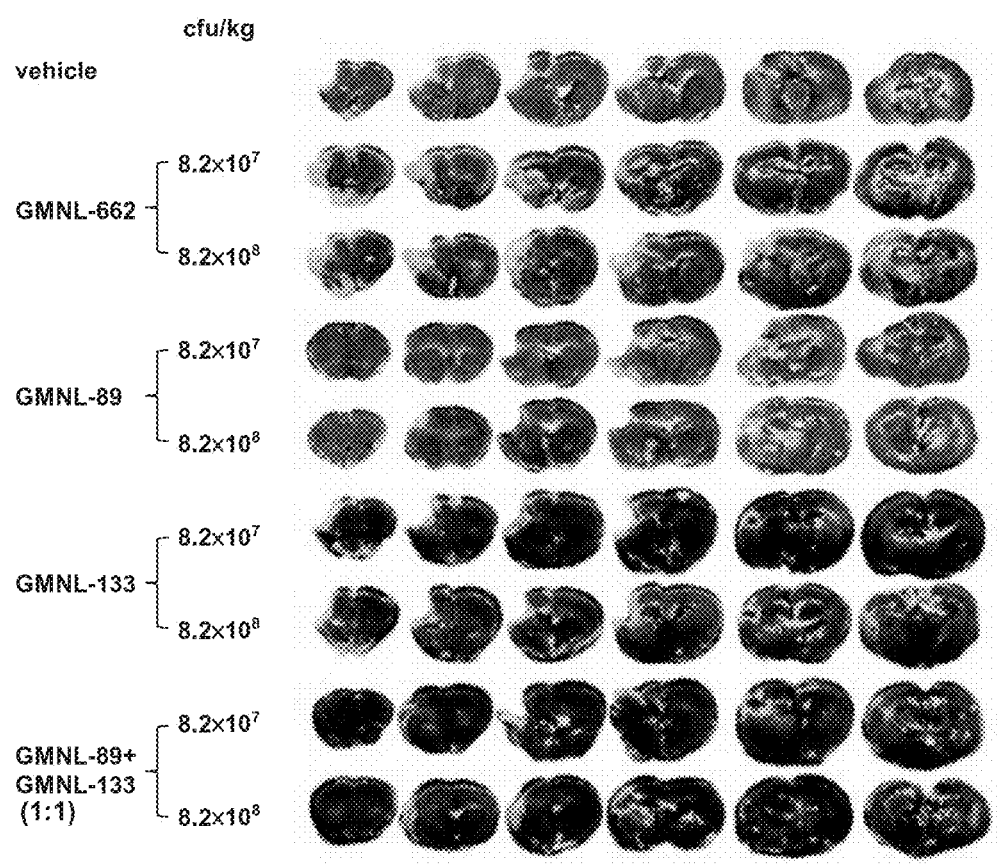
FIG. 2 shows the effects of different probiotics on the infarct zone caused by ischemic stroke.
Figure 3:
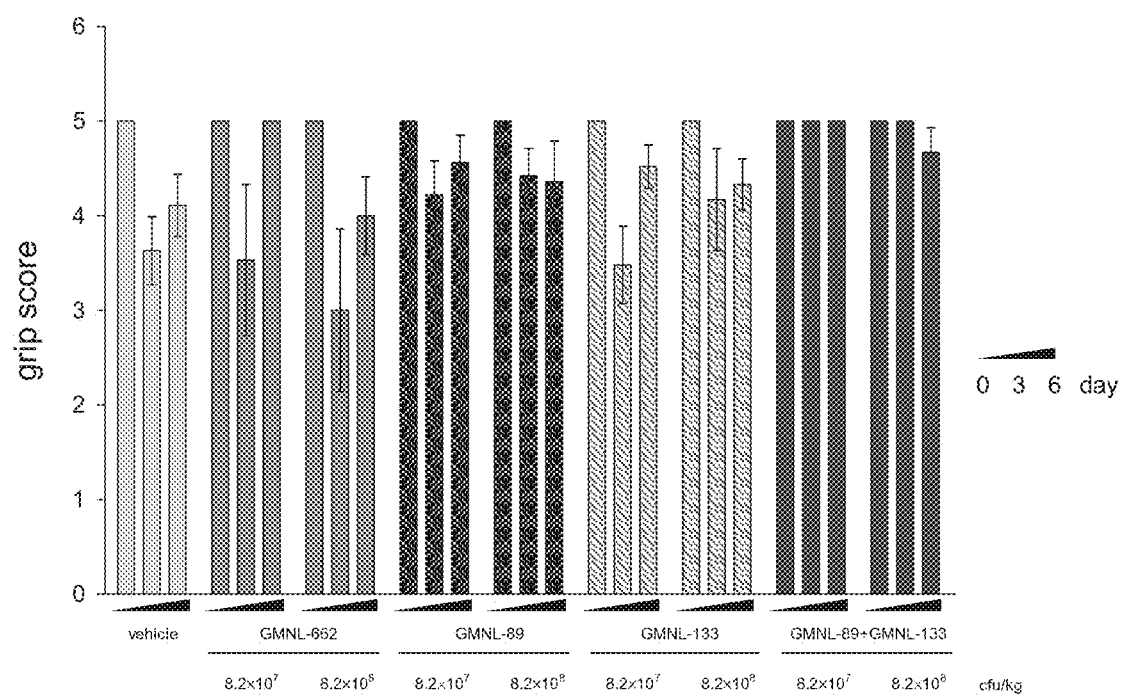
FIG. 3 shows the effects of different probiotics on motor dysfunction caused by ischemic stroke-the Grip Test.

Results:

The study was carried out by following the procedures shown in FIG. 1A and FIG. 1B. The antibiotic water was given for 10 days and then rested for 2 days. Next, gavage feeding of the mice with different doses of a single probiotic strain and probiotic compositions for 5 days to induce stroke. The mice were fed with probiotics for 11 days via gavage after stroke induction and the Grip Test was used to examine the motor function of the mice during this period. The mice were sacrificed on Day 12 to allow examination of the infarct zone in the brain. The results of cerebral infarction were calculated based on the white area and the defects in the tissue section of the brain of FIG. 2, and the results are shown in Table 2. The defects are the results of liquefaction after infarction and the motor function is evaluated by the grip strength test and the results are shown in FIG. 3. The effects of different probiotic groups on the infarct zone in the brain caused by ischemic stroke are described below.

TABLE 2

The effects of different probiotic groups on the infarct zone in the brain caused by ischemic stroke

| groups | n | cfu/kg mice | infarct volumn mean ± SEM |
|---|---|---|---|
| vehicle | 17 | 0 | 38.2 ± 2.33 |
| GMNL-662 | 5 | $8.2 \times 10^7$ | 34.0 ± 2.73 |
|  | 5 | $8.2 \times 10^8$ | 33.7 ± 1.10 |
| GMNL-89 | 8 | $8.2 \times 10^7$ | 37.8 ± 4.94 |
|  | 9 | $8.2 \times 10^8$ | 25.9 ± 2.41* |
| GMNL-133 | 7 | $8.2 \times 10^7$ | 25.4 ± 1.82* |
|  | 6 | $8.2 \times 10^8$ | 27.8 ± 2.61* |
| GMNL-89+ | 2 | $8.2 \times 10^7$ | 19.0 ± 4.42* |
| GMNL-133 | 5 | $8.2 \times 10^6$ | 21.5 ± 1.31* |

*L. plantarum* GMNL-662 group: Gavage feeding of the mice with high-dose or low-dose *L. plantarum* GMNL-662 did not significantly reduce the infarct zone in the mice (Table 2) and showed poorer improvement in the motor function of the mice with stroke (FIG. 3).

*L. reuteri* GMNL-89 group: Gavage feeding of the mice with low-dose ($8.2 \times 10^7$ CFU/kg mice) *L. reuteri* GMNL-89 did not reduce the infarct zone in the mice (Table 2); whereas gavage feeding of the mice with high-dose ($8.2 \times 10^8$ CFU/kg mice) of *L. reuteri* GMNL-89 significantly reduced the infarct zone in the brain of these mice (Table 2, *: P<0.05, compared with vehicle), and the motor function also showed a better recovery (FIG. 3).

*L. paracasei* GMNL-133 group: Gavage feeding of the mice with high-dose ($8.2 \times 10^7$ CFU/kg mice) or low-dose ($8.2 \times 10^8$ CFU/kg mice) of *L. paracasei* GMNL-133 significantly reduced the infarct zone in the brain of these mice (Table 2); gavage feeding of the mice with high-dose *L. paracasei* GMNL-133 showed a better improvement in the motor function of the mice with stroke (FIG. 3).

The *L. reuteri* GMNL-89 group and *L. paracasei* GMNL-133 group: A subsequent protective stroke test was carried out by using a multi-strain composition of *L. reuteri* GMNL-89 and *L. paracasei* GMNL-133. The results indicated that the multi-strain composition of high-dose ($8.2 \times 108$ CFU/kg mice) and low-dose ($8.2 \times 107$ CFU/kg mice) of GMNL-89 and GMNL-133 (1:1) had a better protective effect on reducing the infarct zone in the mice as well as improving the motor function in the mice with stroke when compared with the treatment of a single bacterial strain at the same dose level (Table 2, FIG. 3), indicating that the multi-strain composition has an additive effect and offers the best protection against injury caused by ischemia and reperfusion in the brain.

The effects of different probiotic groups on the intestinal microbiota caused by ischemic stroke are described below.

From the results of intestinal microbiota analysis, the feces of the mice in the disease induction group contained a higher level of *Bacteroides* (*Bacteroidetes* richness: 76.46%) and a lower level of *Firmicutes* (*Firmicutes* richness: 23.27%). On the other hand, gavage feeding with GMNL-89, GMNL-133 or the multi-strain composition (GMNL-89+GMNL-133) relatively reduced the *Bacteroides* richness and increased the *Firmicutes* richness (FIG. 4).

Figure 4:
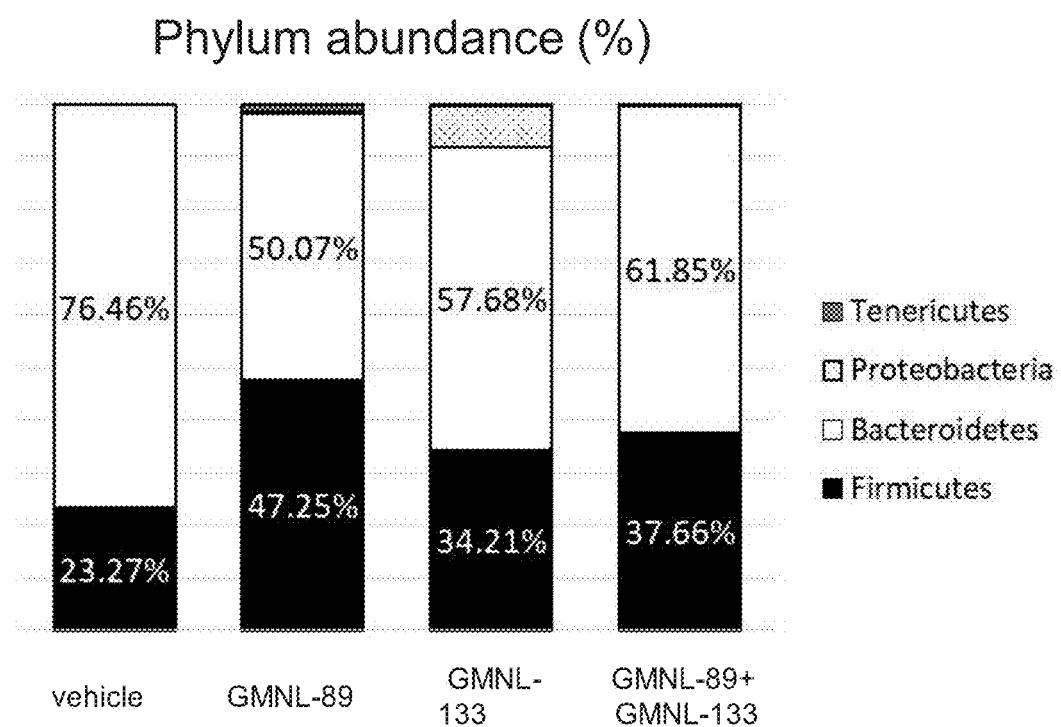
FIG. 4 shows the results of flora richness analysis in mice with ischemic stroke treated with different groups of probiotics (at phylum level).

According to the results of bacterial phylum analysis, the regulation of the intestinal microbiota by the GMNL-89 group, the GMNL-133 group and the multi-strain composition (GMNL-89+GMNL-133) were not completely the same (FIG. 4). From the analysis of *Lactobacillus* richness, the result indicated that the GMNL-89 group (0.26%) was higher and the GMNL-133 group (0.18%) was lower, but both were significantly higher compared with the disease induction group (0.06%) (Table 3). Past studies have found that the richness of relevant good bacteria will decrease when ischemic stroke occurs. According to the results of the microbiota analysis of this study, the richness of the two good bacteria, *Ruminococcaceae* and *Oscillospira*, in the disease-induction group were significantly lower than the three groups treated with probiotics (Table 3), indicating that gavage feeding with GMNL-89, GMNL-133 or GMNL-89+ GMNL-133 may achieve the protective effect against stroke damage through the two strains of good bacteria, while there was no significant change in the bad bacteria based on the analysis, which may be related to the consumption of antibiotic water before the study. Therefore, it can be inferred from these results that *Lactobacillus reuteri* GMNL-89 and *Lactobacillus paracasei* GMNL-133 achieve the protective effect against the symptoms of ischemic stroke by regulating and increasing good bacteria in the intestinal tract, stabilizing the intestinal immune response, and inhibiting the production of excessive inflammatory response factors.

TABLE 3

Analysis of the effects of different probiotics on the richness of good and bad bacteria

| | abundance (%) | | | |
|---|---|---|---|---|
| | vehicle | GMNL-89 | GMNL-133 | GMNL-89 + GMNL-133 |
| *Lactobacillus* | 0.06% | 0.26% | 0.18% | 0.12% |
| *Ruminococcaceae* | 4.20% | 11.57% | 7.00% | 7.71% |
| *Oscillopira* | 3.00% | 7.21% | 5.93% | 6.60% |
| *Bacteroides* | 0.00% | 0.20% | 0.00% | 0.01% |
| *Haemophilus* | 0.00% | 0.00% | 0.00% | 0.00% |
| *Shuttleworthia* | 0.03% | 0.03% | 0.01% | 0.01% |
| *Faecalibacterium* | 0.00% | 0.00% | 0.00% | 0.00% |

In conclusion, the probiotic composition of the present invention can prevent stroke and ameliorate the health of an individual after a stroke, including:

1) reducing the size of the infarct zone in the brain,
2) restoring the motor function (such as grip strength),
3) ameliorating intestinal microbiota, including the increase of the good bacteria such as *Ruminococcaceae* and *Oscillospira*;

and achieve the effects of preventing stroke and ameliorating the severity of stroke.

What is claimed is:

1. A method used for ameliorating a severity of a stroke, comprising administrating a probiotic composition, wherein the probiotic bacterial strain is selected from the groups consisting of *Lactobacillus reuteri* GMNL-89 with the deposition number of CCTCC M207154, and *Lactobacillus paracasei* GMNL-133 with the deposition number of CCTCC M2011331.

2. The method as claimed in claim 1, wherein ameliorating stroke is ameliorating ischemic stroke.

3. The method as claimed in claim 1, wherein ameliorating stroke is ameliorating cerebral infarction caused by stroke.

4. The method as claimed in claim 1, wherein ameliorating stroke is ameliorating the recovery status of the patient after a stroke.

5. The method as claimed in claim 1, wherein the recovery status of the patient is motor function.

6. The method as claimed in claim 1, wherein the dose of the probiotics is $1\times10^7 \sim 1\times10^{10}$ live bacteria per day.

* * * * *